US011690801B2

(12) United States Patent
Edwards

(10) Patent No.: US 11,690,801 B2
(45) Date of Patent: *Jul. 4, 2023

(54) ADHERENT ORAL PHARMABIOTIC DELIVERY STRIP

(71) Applicant: Steven J. Edwards, Laguna Niguel, CA (US)

(72) Inventor: Steven J. Edwards, Laguna Niguel, CA (US)

(*) Notice: Subject to any disclaimer, the term of this patent is extended or adjusted under 35 U.S.C. 154(b) by 247 days.

This patent is subject to a terminal disclaimer.

(21) Appl. No.: 17/344,062

(22) Filed: Jun. 10, 2021

(65) Prior Publication Data

US 2021/0299037 A1    Sep. 30, 2021

Related U.S. Application Data

(63) Continuation of application No. 16/684,255, filed on Nov. 14, 2019, now Pat. No. 11,058,634.

(60) Provisional application No. 62/769,502, filed on Nov. 19, 2018.

(51) Int. Cl.
| A61F 13/00 | (2006.01) |
| A61K 9/00 | (2006.01) |
| A61K 35/742 | (2015.01) |
| A61K 31/047 | (2006.01) |
| A61K 35/747 | (2015.01) |
| A61K 31/736 | (2006.01) |
| A61K 35/745 | (2015.01) |

(52) U.S. Cl.
CPC ............ *A61K 9/006* (2013.01); *A61K 31/047* (2013.01); *A61K 31/736* (2013.01); *A61K 35/742* (2013.01); *A61K 35/745* (2013.01); *A61K 35/747* (2013.01)

(58) Field of Classification Search
None
See application file for complete search history.

(56) References Cited

U.S. PATENT DOCUMENTS

| 4,876,092 A | 10/1989 | Mizobuchi et al. |
| 5,578,315 A | 11/1996 | Chien et al. |
| 5,894,017 A | 4/1999 | Sagel et al. |
| 6,419,903 B1 | 7/2002 | Xu et al. |
| 6,455,030 B2 | 9/2002 | Saito et al. |
| 7,500,984 B2 | 3/2009 | Fuisz et al. |
| 7,946,296 B2 | 5/2011 | Wrenn et al. |
| 8,021,696 B2 | 9/2011 | Loewy et al. |
| 8,420,376 B2 | 4/2013 | Alenfall et al. |
| 8,586,029 B2 | 11/2013 | Kasper et al. |
| 8,691,214 B2 | 4/2014 | Alenfall et al. |
| 8,701,671 B2 | 4/2014 | Kovarik |
| 8,911,770 B2 | 12/2014 | Grassi |
| 9,192,572 B2 | 11/2015 | Skigen |
| 9,326,924 B1 | 5/2016 | Fourre et al. |
| 9,636,196 B2 | 5/2017 | Hillman |
| 11,058,634 B2 * | 7/2021 | Edwards ............... A61K 36/28 |
| 2007/0098744 A1 | 5/2007 | Knorr et al. |
| 2011/0104239 A1 | 5/2011 | Knutsen et al. |
| 2015/0297642 A1 | 10/2015 | Borody |
| 2017/0232048 A1 | 8/2017 | Edwards |

FOREIGN PATENT DOCUMENTS

WO    2018/169296    9/2018

OTHER PUBLICATIONS

Lee, Sung-Hoon and Young-Jae Kim, "A comparative study of the effect of probiotics on cariogenic biofilm model for preventing dental caries," Arch Microbiol, Jun. 12, 2014, 9 pages, Springer-Verlag Berlin Heidelberg.
MacDonald, Kyle W., "The Role of *Streptococcus salivarius* as a Modulator of Homeostasis in the Oral Cavity," (2015), University of Western Ontario—Electronic Thesis and Dissertation Repository, Paper 2816, 94 pages.
Sherburne, Morgan, "Fighting cavities could one day be as easy as taking a pill, research shows," https://news.ufl.edu/articles/2016/03/fighting-cavities-could-one-day-be-as-easy-as-taking-a-pill-research-shows.html, Mar. 10, 2016, 3 pages, University of Florida, Gainesville, FL.
Sintim, Herman O. and Ulvi Kahraman Gürsoy, "Biofilms as 'Connectors' for Oral and Systems Medicine: A New Opportunity for Biomarkers, Molecular Targets, and Bacterial Eradication," OMICS a Journal of Integrative Biology, 2016, vol. 20, No. 1, pp. 3-11, Mary Ann Liebert, Inc.
Söderling, Eva et al., "The Effect of Xylitol on the Composition of the Oral Flora: A Pilot Study," European Journal of Dentistry, Jan. 2011, vol. 5, pp. 24-31.
Tahmourespour, Arezoo, "Probiotics and the Reduction of Dental Caries Risk," Contemporary Approach to Dental Caries, Mar. 2012, pp. 271-288.
Wescombe, Philip A. et al., "Developing Oral Probiotics From *Streptococcus salivarius*," Future Microbial, 2012; 7(12): 1355-1371.

(Continued)

*Primary Examiner* — Albert M Navarro
(74) *Attorney, Agent, or Firm* — Stetina Brunda Garred and Brucker

(57) ABSTRACT

An oral pharmabiotic system is disclosed for improving oral, dental, and systemic health by repopulating and reshaping the flora within a patient's oral environment in a manner that overcomes the deficiencies of prior oral probiotic products. By formulating the pharmabiotic system as a strip for adhesive placement within a patients' oral cavity, preferably against the buccal mucosa, alveolar mucosa, oral labial mucosa, or a dental appliance, and configuring the parameters of the strip such that neither disadhesion nor complete dissolution occurs for at least a period of at least three hours during daytime use and at least six hours during nighttime use, the probiotic payload contained within may remain in the oral cavity for a sufficient length of time required for the probiotics to activate, replicate, and displace existing harmful oral pathobiotics.

22 Claims, 1 Drawing Sheet

(56) References Cited

OTHER PUBLICATIONS

Yao, Suellan Go and James Burke Fine, "Probiotics for Bacterial Disease Treatment in the Oral Environment," http://aap.cdeworld.com/courses/4911-Probiotics_for_Bacterial_Disease_Treatment_in_the_Oral_Environment?hq_e=el&hq_m=3769923&hq_l=3&hq_v=6bba2ea2c9, May 2015, 6 pages, American Academy of Periodontology.

Anderson, M.H. and W. Shi, "A Probiotic Approach to Caries Management," Pediatric Dentistry, 2006, 28:2, pp. 151-153.

Bai, K. Yellamma and B. Vinod Kumar, "Tonsillolith: A polymicrobial biofilm," Medical Journal Armed Forces India, Jul. 2015, vol. 71, Supplement 1, pp. S95-S98.

Stoodley, Paul et al., "Tonsillolith: not just a stone but a living biofilm," https://www.ncbi.nlm.nih.gov/pubmed/19716006, Otolaryngol Head Neck Surg. Sep. 2009;141(3), abstract only.

Ferrer, Maria D. et al., "A pilot study to assess oral colonization and pH buffering by the probiotic *Streptococcus dentisani* under different dosing regimes," https://www.ncbi.nlm.nih.gov/pubmed/31531771, Odontology, Sep. 17, 2019, Abstract only.

Allaker, Robert P. and Abish S. Stephen, "Use of Probiotics and Oral Health," Current Oral Health Reports, Oct. 19, 2017, vol. 4, pp. 309-318, https://doi.org/10.1007/s40496-017-0159-6.

Kazor, C. E. et al., "Diversity of Bacterial Populations on the Tongue Dorsa of Patients with Halitosis and Healthy Patients," Journal of Clinical Microbiology, Feb. 2003, vol. 41, No. 2, pp. 558-563, American Society for Microbiology.

Loesche, Walter J., "Chapter 99: Microbiology of Dental Decay and Periodontal Disease," Medical Microbiology, 4th edition, 1996, University of Texas Medical Branch at Galveston, Texas, https://www.ncbi.nlm.nih.gov/books/NBK8259/.

Mahasneh, Sari A. and Adel M. Mahasneh, "Probiotics: A Promising Role in Dental Health," Dentistry Journal, Sep. 27, 2017, vol. 5,4 26, 10 pages.

U.S. Department of Health and Human Services, "Oral Health in America: A Report of the Surgeon General," 2000, U.S. Department of Health and Human Services, National Institute of Dental and Craniofacial Research, National Institutes of Health, Rockville, Maryland, pp. 6-7 and 109-110.

Copenheaver, Blaine R., "International Search Report and Written Opinion of the International Searching Authority," PCT Appln. No. PCT/US2019/061861, dated Jan. 24, 2020, ISA/US, Alexandria, Virginia, 8 pages.

Banas, Jeffrey A., and Eric T. Popp, "Recovery of Viable Bacteria from Probiotic Products that Target Oral Health," NIH-PA Author Manuscript, National Institute of Health, Sep. 2013, 7 pages.

Bollen, Curd ML, and Thomas Beikler, "Halitosis: the multidisciplinary approach," International Journal of Oral Science, 2012, pp. 55-63.

Bonifait, Laetitia et al., "Probiotics for Oral Health: Myth or Reality?", JCDA, www.cda-adc.ca/jcda/vol-75/issue-8/585.html, Oct. 2009, vol. 75, No. 8, pp. 585-590.

Burton, J.P. et al., "A preliminary study of the effect of probiotic *Streptococcus salivarius* K12 on oral malodour parameters," Journal of Applied Microbiology, 2006, pp. 754-764, The Society for Applied Microbiology.

Cagetti, Maria Grazia et al., "The Use of Probiotic Strains in Caries Prevention: A Systematic Reveiw," Nutrients, Jul. 2013, www.mdpi.com/journal/nutrients, pp. 2530-2550.

Cannon, Mark L. et al., "Retrospective Review of Oral Probiotic Therapy," The Journal of Clinical Pediatric Dentistry, 2019, vol. 43, No. 6, 5 pages.

Carroll, Ian M. and Nitsan Maharshak, "Enteric bacterial proteases in inflammatory bowel disease-pathophysiology and clinical implications," World Journal of Gastroenterology, Nov. 21, 2013, vol. 19, Issue 43, 7531-7543, http://www.wjgnet.com/1007-9327/full/v19/i43/7531.htm.

Chen, Shui-Jiao et al., "Ulcerative colitis as a polymicrobial infection characterized by sustained broken mucus barrier," World Journal of Gastroenterology, Jul. 28, 2014, vol. 20, Issue 28, 9468-9475, http://www.wjgnet.com/1007-9327/full/v20/i28/9468.htm.

Deogade, Suryakant C., "Probiotics: Contributions to Oral and Dental Health," OHDM, Jun. 2015, vol. 14, No. 3, pp. 145-154.

Di Pierro, Francesco et al., "Use of *Steptococcus salivarius* K12 in the prevention of streptococcal and viral pharyngotonsillitis in children," Drug Healthcare and Patient Safety, Feb. 13, 2014, 15-20, Dove Medical Press Limited.

Featherstone, J.D. et al., "Novel Anticaries and Remineralization Agents: Future Research Needs," Journal of Dental Research, 2018, vol. 97(2), 125-127, International & American Associations for Dental Research 2018, Sage Publishing.

Fiedler, Tomas et al., "Protective Mechanisms of Respiratory Tract Streptococci against *Streptococcus pyogenes* Biofilm Formation and Epithelial Cell Infection," Applied and Environmental Microbiology, Feb. 2013, vol. 79, No. 4, 1265-1276, American Society for Microbiology.

Gupta, Vivek and Bhavana Gupta, "Probiotics and Periodontal Disease: A Current Update," Journal of Oral Health and Community Dentistry, 2010, 4(Spl), 35-37.

Hajishengallis, George et al., "The Keystone Pathogen Hypothesis," Nat Rev Microbiol. Author manuscript, Apr. 1, 2013, PMC, National Institute of Health, 17 pages.

Landers, Bill, "Oral bacteria: How many? How fast?", https://www.rdhmag.com/infection-control/water-safety/article/16404976/oral-bacteria-how-many-how-fast, Jul. 1, 2009, 4 pages, Endeavor Business Media, LLC.

Lawande, Dr. Sandeep, "Probiotics for Management of Periodontal Disease: A Novel Therapeutic Strategy?", IOSR Journal of Pharmacy, Jul.-Aug. 2012, vol. 2, Issue 4, pp. 41-46.

\* cited by examiner

Initial placement above posterior molars. Adheres in 15 seconds.
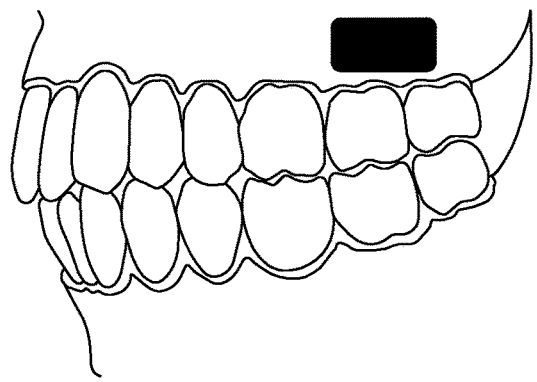
Initial placement
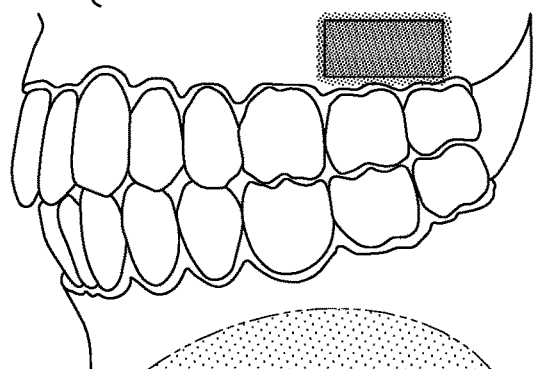
15 minutes
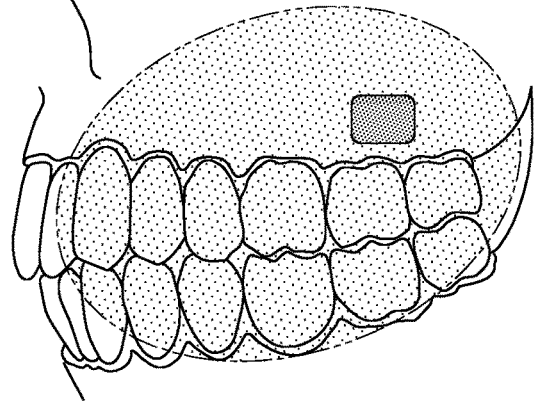
3 hours
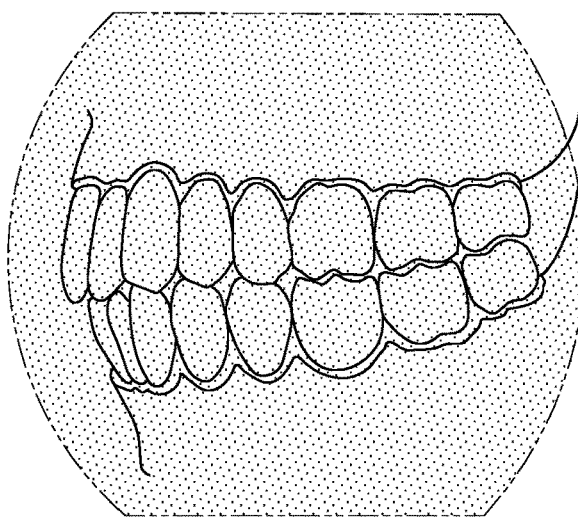
6 to 8 hours

ADHERENT ORAL PHARMABIOTIC DELIVERY STRIP

CROSS-REFERENCE TO RELATED APPLICATIONS

This application is a continuation of U.S. patent application Ser. No. 16/684,255, filed Nov. 14, 2019, now U.S. Pat. No. 11,058,634, issued Jul. 13, 2021, which claims the benefit of U.S. Provisional Application No. 62/769,502, filed Nov. 19, 2018 and entitled ADHERENT ORAL PHARMABIOTIC DELIVERY STRIP, the contents of which are expressly incorporated herein by reference.

STATEMENT RE: FEDERALLY SPONSORED RESEARCH/DEVELOPMENT

Not Applicable

BACKGROUND

1. Technical Field

The present disclosure relates generally to the field of oral pharmabiotics. More particularly, the present disclosure relates to novel systems for delivering oral pharmabiotics.

2. Related Art

In the United States, dental problems are the second most commonly occurring medical condition, trailing only the common cold. Dental caries (tooth decay and cavities) and periodontal disease are the two most substantial oral health problems in the United States, and are among the most common preventable chronic diseases. In fact, dental caries are the most common preventable chronic disease in children.

Poor oral health has also been linked as a potential causative agent to systemic medical conditions, including Alzheimer's, stroke, cardiac disease, pancreatitis, esophageal cancer, pneumonia, reproductive conditions, intestinal disease, and diabetes, with diabetes and periodontal disease being shown to exacerbate one another. Thus, improving oral health may improve overall systemic health. The oral/systemic link, whereby breaks in the oral epithelium permit dental pathobiotics and their harmful byproducts to spread throughout the body via the bloodstream and lymphatic system, may be at the root of this causation. As these diseases are among the costliest to our public health system, even if an oral health measure may only result in marginal reductions to their prevalence, that measure may still be extremely cost-effective.

Furthermore, from a public health standpoint, improving the general oral health of the American population as a whole through preventive measures is by far one of the most cost-effective measures available. However, despite substantial technological advances in the fields of restorative and prosthetic dental care, such as the use of advanced materials for implants and digital CAD/CAM prosthetic technology, very little has changed over the past 20 years in the field of preventive dental care. As a result, even the most meticulously performed restorations still tend to prematurely fail, requiring successive restorations. This is because the existing paradigm for preventive care is insufficient to combat the root causes of oral disease.

It is therefore important that new methods of preventive dental care are developed. Such methods must be proactive rather than reactive, scientific and evidence-based, and must be aimed at breaking the oral/systemic link. In this regard, one promising route forward lies at the intersection of the fields of probiotics and dentistry.

BRIEF SUMMARY

Thus, there is a need in the art for improved systems and methods for preventive oral health which address the root cause of dental disease, rather than merely managing those root causes. Furthermore, such improved systems and methods must permit ready and simple patient compliance. In this regard, a novel adherent, place and forget, oral pharmabiotic delivery strip is contemplated. The newly coined term "densysbiotic" is proposed for the strip to indicate probiotic use for dental and systemic health, because oral health is linked to systemic health.

To successfully repopulate and/or reshape the flora within a patient's oral cavity, an oral pharmabiotic must be retained for a substantial period of time within the oral cavity, and must remain within the oral cavity during all sorts of potential oral activities, including salivation, chewing, drinking, smoking, etc. Likewise, the oral pharmabiotic product must be suitable for placement during sleep without posing a choking hazard if dislodged or causing discomfort due to excessive width or thickness. In this regard, a flexible adhesive strip for buccal placement represents an elegant solution, with the flexibility and the strip configuration providing a large, malleable surface area for maximum adherence to an irregular oral surface while maintaining a low profile so as to not cause discomfort or risk choking if disadhered. In this regard, a strip formulation may maximize patient acceptance and compliance, which is a major barrier to preventive oral health measures.

Ordinary applications of dentifrices in combination with probiotics tend to fail to reshape existing oral biofilms, the contents of which are up to a thousand times more difficult to kill than planktonic, free floating organisms in saliva. Furthermore, huge reservoirs of pathobiotics reside on the posterior dorsal tongue surface, within the tonsillar crypts, in the throat, and in deep periodontal pockets, all of which are difficult to reach with existing preventive oral health measures. It is virtually impossible to floss, brush, or gargle away these reservoirs. These pockets of organisms are highly resistant to being dislodged via applications of dentifrices in combination with short term probiotics, which tend to fail to reshape existing oral biofilms. Time release, long duration probiotics may represent one route to resolving this issue.

Conventional dissolvable strips dissolve too rapidly to be retained in the oral cavity for a sufficient amount of time for the bacterial payload to be released and maintained in the oral cavity so as to effectively reshape the patient's oral flora. Tests have shown that freeze-dried live organisms must be retained in the mouth for at least three hours without being swallowed to achieve intraoral growth of significance, otherwise a too-rapid dissolution of a strip product would result in the organisms primarily ending up in the gut. Preferably, the oral pharmabiotic product should be retained for six hours during daytime use, and for up to eight hours during nighttime use.

Finally, because many dental problems take years to develop and provide few noticeable symptoms until the problems are advanced, it should be appreciated that an effective oral pharmabiotic should have a feedback mechanism to satisfy the user that the product is performing satisfactorily. Such feedback mechanisms include halitosis (oral malodor) and xerostomia (dry mouth), the relief of which may reward patients and substantially improve continued patient compliance. Thus, it is desirable that an oral pharmabiotic product may also have ancillary oral health benefits in mitigating or eliminating such highly offensive or noticeable conditions.

It is also envisioned that such a strip may contain erythritol as a component. Erythritol is a 4-carbon sugar alcohol that displays similar dental health benefits to xylitol, but is in many respects superior, due to being essentially non-caloric (0.24 cal/gram), well tolerated intestinally, non-toxic to household pets, and may display effectiveness in reducing dental plaque weight and disrupting oral biofilms. Erythritol also has a mouth-cooling and saliva-stimulating effect, increasing the feedback provided to the user so as to improve mouthfeel of the product and patient compliance, as well as reduction of xerostomia.

According to one exemplary embodiment of the present disclosure, a pharmabiotic strip is contemplated, the pharmabiotic strip comprising a carrier matrix, gum Arabic, erythritol, and a probiotic payload having a mass comprising up to 50% of the total mass of the pharmabiotic strip, the probiotic payload comprising freeze-dried live bacteria, at least one of the freeze-dried live bacteria being selected from one or more of: a *Lactobacillus*, a *Bacillus*, a *Streptococcus*, a *Weisella*, a *Bifidobacterium*, an *Enterococcus*, a *Saccharomyces*, and combinations thereof, and wherein the probiotic payload comprises at least 3 billion colony forming units.

The carrier matrix may comprise pullulan. The pharmabiotic strip may also further comprise an additional prebiotic, an additional flavoring agent, or a quorum-sensing inhibitor.

It is contemplated that the pharmabiotic strip may be configured for adherence to a variety of intraoral surfaces, such as the alveolar mucosa, the buccal mucosa, or the oral labial mucosa. It is additionally contemplated that the pharmabiotic strip may be configured for adherence to an oral appliance, such as a retainer, a night guard, a sleep apnea mouth device, a restoration, an implant, dentures, etc.

According to one particular exemplary embodiment, the probiotic payload may comprise *Lactobacillus rhamnosus*, *Bifidobacterium infantis*, and *Lactobacillus reuteri*. According to another exemplary embodiment, the probiotic payload may comprise *Lactobacillus acidophilus*, *Enterococcus faecium*, *Lactobacillus plantarum*, *Bifidobacterium. lactis*, *Bifidobacterium longum*, and *Streptococcus thermophilus*.

It is contemplated that, in embodiments where the pharmabiotic strip further comprises a quorum-sensing inhibitor, the quorum-sensing inhibitor may be selected from one or more of: *Chamaemelum nobile* extract, *Combretum albiflorous* extract, *Laurus nobilis* extract, *Sonchus oleraceus* extract, Quercetin, resveratrol, grape seed extract, garlic extract, vanillin, 3-oxo-N-(2-oxocyclohexyl)dodecanamide, Curcumin, and combinations thereof.

It is additionally contemplated that, in embodiments where the pharmabiotic strip further comprises an additional prebiotic, the additional prebiotic may be selected from one or more of: Inulin, Lactoferrin, L arginine, Pectin, and combinations thereof.

It is further contemplated that, in embodiments where the pharmabiotic strip further comprises an additional flavoring agent, the additional flavoring agent may be selected from one or more of: isomalt, spearmint, *stevia*, monkfruit extract, cranberry extract, blueberry extract, and combinations thereof.

It is contemplated that various manufacturing processes may be utilized during the manufacture the presently contemplated pharmabiotic strip. Such manufacturing processes may include, for example, a solvent casting process, a spraying process, a hot extrusion process, a 3-D printing process,

BRIEF DESCRIPTION OF THE DRAWINGS

These and other features and advantages of the various embodiments disclosed herein are better understood with respect to the following descriptions and drawings, in which:

FIG. 1 is a sequence of illustrations showing placement of an oral pharmabiotic delivery strip for nighttime use against a patient's alveolar mucosa and the process of subsequent dissolution over a six to eight-hour period.

DETAILED DESCRIPTION

According to various aspects of the present disclosure, various embodiments of adherent oral pharmabiotic delivery strips and methods of manufacturing and using such delivery strips are contemplated. In an exemplary embodiment, an adherent oral pharmabiotic delivery strip may be formed via solvent casting wherein freeze-dried live probiotic bacteria are mixed in a liquid along with all other components of the strip, with the resulting viscous material being fed through a conveyor belt, leveled, and run through a series of drying ovens to evaporate the solvent to produce a strip of consistent thickness, typically around 2 mm, and thereafter cut into rectangular strips or other shapes and packaged. However, a number of other manufacturing methods and other variations in components may also be utilized, as herein described. For example, dead organisms or the metabolites of organisms alone may be utilized instead of live probiotics to take advantage of the postbiotic effect.

In prior art oral probiotic tablets or strips, as they dissolve in the mouth, the excipients merely dissociate away, and the organisms freely float around in saliva as planktonic organisms and are swallowed. The patient unconsciously moves the tablet around in the mouth and thus speeds up the dissolution, or chews it and swallows it almost immediately. As a result, most of the organisms in a typical tablet are swallowed and are gone from the mouth in about 15 minutes. While patients may be instructed to let tablets or strips dissolve slowly, most patients end up chewing them and swallowing them too soon anyway. Therefore, many billions of organisms must be used at the outset in order to supply some leftovers after many die and most of the rest are merely swallowed. Also, people use probiotic tablets during waking hours because it may be dangerous to sleep with a loose tablet floating about in the mouth, and even an adherent lozenge or tablet may have some safety concerns. Thus, a low-profile strip is more desirable than a high-profile lozenge or tablet. Furthermore, about 28% of people cannot tolerate pills, lozenges, nor tablets in their mouth, as they fear choking. Therefore, a strip delivery method can benefit many more people than a pill, tablet, or lozenge.

The prior art, non-strip approach is inefficient, haphazard, inconsistent, wasteful, expensive, and especially limiting in terms of types of organisms to be used and quantity required. Because so many billions of organisms are needed at the start, it is expensive to use more than a few types of organisms, thus limiting choices and potential synergistic effects of having organism diversity. For oral probiotics, diversity is desirable because microbes are communal and work best in groups. In addition, many organisms are synergistic together. Diversity is also essential for oral heath because of the mouth's numerous types of niches and the vast conditions to which the oral cavity is exposed. But because of needing so many billions at the outset, the concept of using potentially synergistic combinations of various types of organisms is prohibitively expensive. As a result, most prior art dental probiotics are limited to just one or a few types of organisms. Furthermore, if the sleeping hours could be utilized for probiotic delivery, the organisms have an exponentially greater chance for growth, colonization, and population. This is because salivary flow diminishes during sleep and the mouth is essentially like an incubator overnight while sleeping.

The ideal life cycle of a freeze-dried intraoral probiotic organism is as follows:

Upon a tablet or strip being exposed to saliva, the strip's outer-lying organisms begin rehydrating. Each freeze-dried organism requires about 4 minutes to rehydrate, and then an additional 2.5 hours to grow and replicate. This is the reason for the 3-hour minimum strip dissolution rate. If a strip or lozenge is left to dissolve on its own, it may take anywhere from 2 minutes to 6 hours, or even 8 hours, for the product to totally dissolve, depending upon the product's thickness, density, excipients, and whether it is chewable, fastmelt, or substantively orally adherent. For example, In the case of the prior art adherent Orchestra™ Dental Probiotics, often the adhered lozenge was still dissolving after 8 hours. Although it is very rare to find any dental products still actively working in the mouth after 15 minutes, a dissolution time of greater than 8 hours may be counterproductive and sometimes even annoying to consumers. Most patients prefer a night-time dental product to be completely dissolved by the time they awaken after 6 or 8 hours.

In the case of chewable tablets, powders, drinks, etc., the entire product is often swallowed within 2 minutes, and certainly is gone by 15 minutes. Furthermore, most typical dental probiotic tablet/lozenge excipients tend to be slightly gritty or chalky and provide an unpleasant mouth feel. Therefore, most patients ultimately want to swallow such particulates sooner than later. Tablets that are manufactured with fast-melt technology have a smooth, creamy texture and a nice mouth feel, but their rapid dissolution and swallowing from the mouth defeats the purpose of trying to rehydrate and grow microbes and colonize the mouth. Thus, if a dental probiotic product cannot be retained in the mouth for more than at least 4 minutes, the whole point of the probiotic's dental usefulness is thwarted, because the microbes haven't even had a chance to rehydrate, let alone grow and eventually replicate. The organisms can't have any dental benefit if they are down in the lower gut.

Once the organism is rehydrated, it needs to recognize and adapt to its new environment. Adaptation generally requires another 4 to 20 minutes. The total time elapsed at this point is between 8 minutes and 24 minutes. However, by 15 minutes, most typical probiotics are already swallowed. After adaptation, any remaining organisms do not yet immediately grow nor replicate. Instead, they enter a latent phase, called the "lag phase", during which they must repair damaged systems and turn on or off certain genes to get ready to grow and replicate, plus find food while avoiding predators, toxins, enzymes, and immunoglobulins. Some organisms die before completing the lag phase because they are too damaged. The lag phase generally requires at least two hours, so the total time elapsed at this point will generally be from two and a quarter to two and a half hours.

After the lag phase comes the "log phase" in which the surviving organisms replicate logarithmically (exponentially). During the log phase, depending on temperature, food sources, safety, etc., the microorganisms can double in number every 10 minutes to 53 minutes. Most of the organisms in the strip can reach the log phase because the strip will completely disperse and dissolve by a total elapsed time of approximately 3 hours while the user is awake, or by 6 or 8 hours during sleep. During this time the organisms are protected and fed while multiplying, dispersing along with the film-forming excipients, and actively colonizing and populating niches.

After the log phase of rapid replication, the organisms reach a point where there is too much crowding, competition for food, waste products, etc., so they slow down and hibernate, or die. The log phase may also end when the user awakens and starts eating or doing daily oral hygiene routines. If the user is awake the whole time, the log phase becomes interrupted numerous times from eating, talking, smoking, etc.

Turning now to FIG. 1, the process of the dissolution of an exemplary strip following placement is illustrated. To use an adherent oral pharmabiotic delivery strip of the present disclosure during the daytime, a user first selects a time of day wherein there is at least a three-hour period between eating or other oral activities. In the exemplary embodiment, it is preferred that the strip may be adhered to the buccal mucosa, alveolar mucosa, or oral labial mucosa, rather than the cheek epithelium, which is generally too mobile for adequate adherence. In other embodiments, however, it is contemplated that the strip may be adhered to or otherwise configured to be integrated with an oral appliance, which may be, for example but without limitation, a retainer, a night guard, a sleep apnea mouth device, a restoration, an implant, dentures, etc. The process of the dissolution of an exemplary strip following daytime placement is as follows:

After placement of the strip, the following 2.5 hours generally involves the lag phase, whereby the probiotics contained within the strip are activated, repaired, and grow prior to replication. During these 2.5 hours, about 83% of the strip disperses and dissolves because of the high oral activity and saliva flow rate. Some of the strip forms a supplemental biofilm that spreads and carries its payload along with it, while protecting some of the probiotics throughout their entire lifecycle. So, even though the actual strip is dissolving, it doesn't mean the contents are immediately carried away from the intraoral environment. Rather, some of the initially-dissolved strip may remain in a biofilm-like state after 2.5 hours. Also, some of the initial probiotic organisms may stay within the strip's spread-out, biofilm-like material and be available for logarithmic growth by 2.5 hours. Meanwhile, the organisms still remaining within the body of the strip are becoming hydrated and will be coming "on line" for replication shortly after 2.5 hours. Once the organisms are ready, they can reproduce for a half an hour to one and a half hours. Although the strip may visually appear to be completely dispersed and dissolved 3 hours after initial placement, some of its excipients may still be able to remain for about another hour, doing their job of protecting, feeding, and disseminating the probiotic payload.

Nighttime use of an exemplary strip of the present disclosure, which may be specifically adapted for nighttime use, or which may be generic for use at all times of day, may proceed as follows:

After the patient performs their usual pre-bedtime oral hygiene routine, the disclosed pharmabiotic strip is adhered to the buccal mucosa, alveolar mucosa, or oral labial mucosa, preferably the alveolar mucosa. It is additionally contemplated that the pharmabiotic strip may be configured for adherence to an oral appliance, such as a retainer, a night guard, a sleep apnea mouth device, a restoration, an implant, dentures, etc. The minimal amount of cheek movement overnight may prevent the strip from dissolving away as fast as it does during daytime use.

The first 2.5 hours is spent getting the probiotics activated and through the lag phase so they can begin replicating. During these 2.5 hours, about 42% of the strip disperses and dissolves into a supplemental biofilm despite the low saliva flow rate while sleeping. Because during sleep swallowing is minimal, most of the dispersed probiotics are still in the mouth, protected by the supplemental biofilm, and caught between the cheek and the gums.

After 2.5 hours of activation, repair, and growth, the dispersed probiotics and some of the strip-retained probiotics can begin replicating. As more and more of the strip becomes infused with saliva (which is 99.5% water), more and more of the probiotics within the strip reach the log phase. Meanwhile, the dispersed ones are now replicating as well. Due to low saliva flow, growth, replication, and intraoral retention are dramatically greater at night than during daytime—just like in regular dental plaque.

Due to the oral incubator effect, and the prebiotic excipients from the strip, the probiotics can reach fairly high amounts by 6 hours when the strip should be dissolved and dispersed. And since the probiotics would likely be retained for a few more hours after the strip is totally gone, there is even more time for prodigious replication amounts by 8 hours. After 8 hours, the strip becomes like daytime probiotic use; however, the differences are that substantially more probiotics can be produced overnight, and they last longer than daytime use, so have substantially better chance of fully colonizing the mouth.

Around 70 billion organisms reproduce from dental plaque overnight during an 8-hour period, with about 20% (14 billion) of those organisms being of varying pathogenicity, some of which are keystone pathogens that substantially contribute to dental problems. Thus, in order to defeat the problematic organisms, these 14 billion pathogens must preferably be managed by probiotic organisms that selectively kill pathogens as opposed to broad spectrum killing by antibiotics and antiseptics. To meaningfully manage these pathogenic organisms, some of the 14 billion must be displaced over an eight-hour period. It is known in the field of medicine that if one can maintain pathogenic organisms to fewer than 15% of the total organisms in a system, disease can often be avoided or controlled. Thus, a new paradigm in medicine is not to kill germs indiscriminately, but rather to be good stewards of our microbes and to attempt to shift the proportion of pathogenic organisms to around 15% or fewer. To achieve this displacement, between 10 to 17.5 billion probiotic organisms must be added to the intraoral environment over the 8-hour period. This quantity alone could substantially reduce the percentage of the most pathogenic organisms in terms of only total numbers, while also allowing the probiotic organisms significant opportunity to fight the pathogens as they naturally do for space, food, and niches.

In order to produce this number of probiotic organisms during daytime use whereby the strip remains in the mouth for only three hours with a 17% strip dispersion rate at the 2.5-hour mark wherein replication begins, the starting strip may contain at least 52 billion organisms to account for attrition and loss. This is far higher than current prior art probiotic lozenges and tablets, which typically contain at least three billion colony-forming units, with a ⅓ viability rate after 18 months of shelf life. In contrast, for a strip for nighttime use with only a 42% strip dispersion rate at the 2.5-hour mark, a far smaller initial probiotic dose is required.

For a probiotic strip as presently envisioned, it is contemplated that the probiotic payload may comprise up to 50% of the mass of the strip. According to one particular embodiment, such a strip may have dimensions around 8.5 mm×16.5 mm×2.0 mm, for a total volume of 280.5 cubic mm. At a 30% to 50% mass payload, this volume can fit as high as 165.5 billion to 275.7 billion freeze-dried probiotic organisms, which may easily meet the criteria outlined above for a daytime or nighttime strip, for an 18-month shelf life whereby ⅓ of the organisms remain viable. Another specifically contemplated strip may have dimensions of, for example, a length and width of 16.5 mm, and a thickness of 1.0 mm. However, it may be seen that any specific combinations of dimensions may be utilized, so long as the probiotic strip is of sufficient size to carry a sufficient amount of probiotic payload, and will not dissolve when placed in the mouth for a sufficient amount of time for the probiotic payload to activate and replicate. In particular, it may be that the probiotic strip may be substantially larger smaller than these above disclosed dimensions, as long as it contains a sufficient probiotic dose.

It is contemplated that an exemplary set of organisms which may be used as probiotic organisms in the payload of the presently disclosed strips may include a combination of: *Lactobacillus acidophilus, Lactobacillus casei, Lactobacillus fermentum, Lactobacillus helveticus, Lactobacillus paracasei, Lactobacillus plantarum, Lactobacillus reuteri, Lactobacillus rhamnosus, Lactobacillus salivarius, Streptococcus rattus, Streptococcus rattus, Streptococcus oralis, Streptococcus uberis, Streptococcus thermophilus, Streptococcus salivarius* K-12, *Streptococcus salivarius* M-18, *Streptococcus* A-12, *Streptococcus dentisani, Streptococcus mitis, Weisella cibaria, Bacillus subtilis, Bifidobacterium infantis, Bifidobacterium lactis, Bifidobacterium longum, Enterococcus faecium*, and *Saccharomyces boulardii*, and *Bacillus coagulans*.

It is contemplated that the primary periodontal pathogenic organisms targeted for displacement are *Porphyromonas gingivalis, Aggregatibacter actinomycetemcomitans*, and *Fusobacterium nucleatum*, which are keystone pathobiotics for late-onset periodontal problems. Key dental caries pathogens targeted for displacement include *Streptococcus mutans, Streptococcus sobrinus*, and *Candida albicans*. According to one exemplary formulation, a specific synergistic probiotic combination of organisms for the herein contemplated strips may be *Lactobacillus rhamnosus, Bifidobacterium infantis*, and *Lactobacillus reuteri*. According to another exemplary formulation, a combination of *L. acidophilus, Enterococcus faecium, L. plantarum, B. lactis, B. longum*, and *S. thermophilus* may be especially suitable in eradicating *Helicobacter pylori*, which is a substantial contributor to periodontitis as well as cancers of the larynx, pharynx and stomach.

Aside from the probiotic organism payload, the presently contemplated pharmabiotic strips may also comprise other inclusions. For example, it may be desirable to provide ingredients which may serve as quorum-sensing inhibitors, such as Chamomile (*Chamaemelum nobile*) extract, or extracts from *Combretum albiflorous, Laurus nobilis*, or *Sonchus oleraceus*, or Quercetin, resveratrol, grape seed extract, garlic extracts, or vanillin. It may also be desirable to include, for example but without limitation: gum Arabic, which may be acacia seyal or acacia senegal (prebiotic, gumming, remineralization), Sodium alginate (gumming, film-forming, hydrogel, time-release), Inulin (prebiotic, sweetener), Spearmint (flavor), Lactoferrin (preservative, prebiotic, iron chelator), Probiferrin (stabilized lactoferrin), omega antioxidants, Betaine (biofilm degradation), L arginine (prebiotic, amino acid, alkaline pH regulator), Monkfruit extract (sweetener), *Stevia* (sweetener), Wellmune (baker's yeast cell wall beta-glucan), Staimune (*Bacillus coagulans* BC30 killed cell walls), probiotic growth medium supernatant, Lactoperoxidase (antibacterial), HPMC K15 (adhesive, gumming, time release), Amelogenin (enamel development peptide), Chitosan (adhesive, tooth remineralization), arginine bicarbonate+calcium carbonate (tooth desensitizer), alpha-tricalcium phosphate (tooth remineralizer), Taurine (osmoprotectant, immune system enhancer, stimulant), Caffeine (stimulant), *Gingko biloba* (stimulant), L. Theanine (relaxant, sleep aid), Melatonin (relaxant, sleep aid), cranberry extract, blueberry extract, beta carotene (antioxidant), isomalt (cooling effect), Microcrystalline cellulose (binder), 3-oxo-N-(2-oxocyclohexyl) dodecanamide (quorum-sensing inhibitor), sodium calciumphosphosilcate (tooth remineralizer and desensitizer), Nanohydroxyapatite (tooth remineralizer and desensitizer), Curcumin (quorum sensing inhibitor), Chios mastic (*H. pylori* eradicator, oral ulcer reduction), Zinc carnosine (oral ulcer reduction, mucosal wall repair, mucosal inflammation attenuation, *H. pylori* inhibitor), L glutamine (mucosal membrane support), Pectin (gumming agent, adhesive, prebiotic), lignite extract (may repair epithelial cell tight junctions and reduce mucosal permeability).

It is contemplated that in an exemplary embodiment, the probiotic payload may comprise at least three billion colony forming units. Colony forming units (CFU) are a measure of viable bacterial cells contained within a sample.

In addition to the use of natural gums and other natural ingredients, the making of oral dissolving film strips may include the use of biocompatible synthetic polymers, lipids, fats, and waxes, to improve the strip-making process. Such ingredients may enhance the formation of films that dry quickly, remain flexible, reduce dissolution in the oral cavity, improve the payload time release, assist intraoral mucosal adhesion, and protect the payload. Exemplary biocompatible ingredients include Polyvinyl alcohol of varying molecular weights, viscosities, and hydrolysis (to fabricate quicker-drying thinner strips without being too viscous to achieve better intraoral time release, intraoral extended release, and lowered water solubility), Polyvinylpyrrolidone (for better film-forming while using natural gums), Magnesium stearate (even a very tiny amount [1% or less per weight] can greatly slow down dissolution so the films can be thinner and dry faster, yet dissolve slower), Glycerol monostearate, Stearyl alcohol, Carnauba wax, and Microcrystalline wax.

It is contemplated that, in exemplary embodiments, all of the inclusions used to form the pharmabiotic are sized at less than 80 microns across at their widest point, which may be seen to result in a product with a smooth mouthfeel without any perceptible "gritty" or "chalky" feel. However, in other embodiments, it may be desired to include inclusions having a greater size, or for all inclusions to be within or below a certain size range.

According to an exemplary embodiment, a strip is manufactured via solvent-casting, wherein all the components of the strip material and the probiotic payload are mixed into a liquid (water or other biocompatible solvent) and the resulting viscous material is fed through a spreader onto a conveyor belt of a releasing medium and levelled out with a doctor blade. The belt and strip solution are run through a series of drying ovens to evaporate the solvent. As the conveyor belt exits the oven, the strip material is peeled off the surface of the releasing medium as a film, which is rolled into constant thickness which may be rolled into a cylinder and stored for later cutting into strips of a desired size. It may also be seen that by controlling the manufacturing parameters, the thickness of the strips may be adjusted. In one embodiment, a strip having a 2 mm thickness may be desirable. In other embodiments, it may be that thinner strips may be desirable, including for example, strips thinner than 0.3 mm or less. It may also be seen that if it is desired to manufacture strips of greater thickness, existing formulated strips may be fused together.

As an alternative to the solvent casting method outlined above, the film-making ingredients alone without the probiotic payload may be manufactured into strips, and the probiotic payload and any other active ingredients may subsequently be sprayed onto the strip prior, during, or after drying. Depending on the parameters of the spraying, the probiotic payload may partially penetrate the strip material and become embedded within, or may only be deposited on the surface.

Another alternative to the above outlined solvent casting method may be to mix the film-making ingredients and fabricate a fully dried roll of uncut film. Following this, the strip material may be fed through a flexographic printing press designed to print a probiotic payload onto the film. In this manufacturing technique, the probiotic payload will only be on the outer surface of the strip, so it may be necessary to incorporate an additional fusion step to embed the probiotic payload on the interior of the final strip. It may thus be seen that the film may be manufactured at only a proportion of the final desired strip thickness, with the final strip being formed as a result of fusing together two or more layers of film.

An additional method for fabrication of the herein contemplated strips may be via a hot extrusion technique whereby the strip materials are mixed together, heated, and the strip fluid is forced through a film-forming die. When the resultant film dries, it may be stored as a rolled film.

It is also contemplated that the herein discussed strips may be manufactured via a 3-D printing technique. Such a technique may result in, for example, strips of varying sizes and thicknesses across their dimensions, which may result in different rates of dissolution.

A further contemplated method of fabrication may be a variation of the above discussed solvent-casting technique where instead of forming the ingredients into a continuous film for rolling and subsequent cutting into strips, the ingredients are deposited directly as round or ovoid drops onto a releasing medium atop flat plastic cards coated with a releasing medium, resulting in fabrication of smaller films which may eventually be die cut into strips. Alternatively, the plastic cards could be overlaid and heat-sealed with an aluminum foil which may seal the perimeter of the deposited film to result in the formation of blister packs. As such, it may also be seen that blister packs may be formed via by depositing the film material into preformed depressions on the plastic cards and subsequently sealing those depression with foil or other materials.

During packaging, strips may be individually packaged, packaged into cassettes for subsequent dispensing, or packaged into bottles for subsequent dispensing. The packaged strips may also be packaged with desiccant materials to aid in improving shelf life.

It is contemplated that the strips of the present disclosure may preferentially include erythritol as a sweetening, mouth-cooling, and saliva-stimulating agent. Further, erythritol may be more effective than other sweetening agents at reducing dental plaque weight, reducing dental plaque acids, reducing counts of *Streptococcus mutans*, and decreasing *Porphyromonas gingivalis* biofilms. Erythritol also has virtually zero intestinal bloating compared to other polyols and is safe for pets.

It is also contemplated that the strips of the present disclosure may be formulated utilizing pullulan as the primary carrier matrix. Pullulan is a nonionic polysaccharide biopolymer that is blood compatible, biodegradable, non-toxic, non-immunogenic, non-mutagenic, noncarcinogenic, impermeable to oxygen, non-hygroscopic, non-reducing, oil-resistant, and easily soluble in both hot and cold water to form clear and viscous solutions and to form thermally stable films with high flexibility, elasticity, anti-static, and adhesion properties.

In an exemplary embodiment, the probiotics may be incorporated within the pullulan carrier matrix along with an inulin prebiotic, gum arabic (acacia), erythritol as a sweetening agent, and isomalt, which serves as an additional sweeter, has mouth-cooling effects, and in some cases serves as a prebiotic. A pharmabiotic strip may subsequently be formulated from these components according to one of the above described methods at a 2.0 mm thickness. However, it may be appreciated that other thicknesses may be utilized in different embodiments, including embodiments in which the thickness at the thickest point are at least 1.0 mm.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the exemplary embodiments.

What is claimed is:

1. A pharmabiotic strip for intraoral adherence, the pharmabiotic strip comprising:
   a carrier matrix;
   gum arabic;
   erythritol; and
   a payload comprising at least one pharmabiotic inclusion selected from one or more of: a freeze-dried live bacteria, a dead bacteria, a bacterial metabolite, and combinations thereof.

2. The pharmabiotic strip of claim 1, wherein the pharmabiotic inclusion comprises a freeze-dried live bacteria selected from one or more of: a *Lactobacillus*, a *Bacillus*, a *Streptococcus*, a *Weisella*, a *Bifidobacterium*, an *Enterococcus*, a *Saccharomyces*, and combinations thereof.

3. The pharmabiotic strip of claim 2, wherein the payload comprises at least 3 billion colony forming units.

4. The pharmabiotic strip of claim 1, wherein the carrier matrix comprises pullulan.

5. The pharmabiotic strip of claim 1, further comprising an additional prebiotic.

6. The pharmabiotic strip of claim 1, further comprising an additional flavoring agent.

7. The pharmabiotic strip of claim 1, wherein the pharmabiotic strip is configured for adherence to the alveolar mucosa.

8. The pharmabiotic strip of claim 1, wherein the pharmabiotic strip is configured for adherence to the buccal mucosa.

9. The pharmabiotic strip of claim 1, wherein the pharmabiotic strip is configured for adherence to the oral labial mucosa.

10. The pharmabiotic strip of claim 1, wherein the pharmabiotic strip is configured for adherence to an oral appliance.

11. The pharmabiotic strip of claim 2, wherein the pharmabiotic inclusion comprises *Lactobacillus rhamnosus*, *Bifidobacterium infantis*, and *Lactobacillus reuteri*.

12. The pharmabiotic strip of claim 2, wherein the pharmabiotic inclusion comprises *Lactobacillus acidophilus*, *Enterococcus faecium*, *Lactobacillus plantarum*, *Bifidobacterium lactis*, *Bifidobacterium longum*, and *Streptococcus thermophilus*.

13. The pharmabiotic strip of claim 1, further comprising a quorum-sensing inhibitor.

14. The pharmabiotic strip of claim 13, wherein the quorum-sensing inhibitor is selected from one or more of: *Chamaemelum nobile* extract, *Combretum albiflorous* extract, *Laurus nobilis* extract, *Sonchus oleraceus* extract, Quercetin, resveratrol, grape seed extract, garlic extract, vanillin, 3-oxo-N-(2-oxocyclohexyl)dodecanamide, Curcumin, and combinations thereof.

15. The pharmabiotic strip of claim 5, wherein the additional prebiotic is selected from one or more of: Inulin, Lactoferrin, L arginine, Pectin, and combinations thereof.

16. The pharmabiotic strip of claim 6, wherein the additional flavoring agent is selected from one or more of: isomalt, spearmint, *stevia*, monkfruit extract, cranberry extract, blueberry extract, and combinations thereof.

17. The pharmabiotic strip of claim 1, wherein the pharmabiotic strip is manufactured via a solvent casting process.

18. The pharmabiotic strip of claim 1, wherein the pharmabiotic strip is manufactured via a spraying process.

19. The pharmabiotic strip of claim 1, wherein the pharmabiotic strip is manufactured via a hot extrusion process.

20. The pharmabiotic strip of claim 1, wherein the pharmabiotic strip is manufactured via a 3-D printing process.

21. A flexible strip for intraoral adherence, the strip comprising:
    a carrier matrix;
    gum arabic; and
    erythritol.

22. The flexible strip of claim 21, further comprising a payload comprising at least one pharmabiotic inclusion selected from one or more of: a freeze-dried live bacteria, a dead bacteria, a bacterial metabolite, and combinations thereof.

* * * * *